(12) United States Patent
Gawad et al.

(10) Patent No.: US 7,294,249 B2
(45) Date of Patent: Nov. 13, 2007

(54) MICROFLUIDIC COMPONENT AND METHOD FOR SORTING PARTICLES IN A FLUID

(75) Inventors: Shady Gawad, Morges (CH); Martin Wüthrich, Neuchâtel (CH); Philippe Renaud, Préverenges VD (CH)

(73) Assignee: Leister Process Technologies (CH)

( * ) Notice: Subject to any disclaimer, the term of this patent is extended or adjusted under 35 U.S.C. 154(b) by 548 days.

(21) Appl. No.: 10/355,320

(22) Filed: Jan. 31, 2003

(65) Prior Publication Data

US 2003/0178310 A1   Sep. 25, 2003

(30) Foreign Application Priority Data

Feb. 1, 2002   (EP) ................... 02002437

(51) Int. Cl.
  *G01N 27/02*   (2006.01)
  *G01F 1/64*   (2006.01)
(52) U.S. Cl. .............. 204/547; 204/643; 422/82.01; 422/82.02; 422/93; 422/98
(58) Field of Classification Search .......... 204/547, 204/643; 422/73, 82.01, 82.02, 93, 98
  See application file for complete search history.

(56) References Cited

U.S. PATENT DOCUMENTS

| 4,326,934 | A  |    | 4/1982  | Pohl |
| 5,489,506 | A  |    | 2/1996  | Crane |
| 6,136,171 | A  |    | 10/2000 | Frazier et al. |
| 6,169,394 | B1 | *  | 1/2001  | Frazier et al. ............ 324/71.4 |
| 6,432,630 | B1 | *  | 8/2002  | Blankenstein .............. 435/4 |
| 6,437,551 | B1 | *  | 8/2002  | Krulevitch et al. ........ 324/71.1 |
| 6,639,404 | B1 | *  | 10/2003 | Stuart-Bruges ............ 324/306 |
| 6,749,736 | B1 | *  | 6/2004  | Fuhr et al. ................. 204/643 |

FOREIGN PATENT DOCUMENTS

| DE | WO 00/00293 | * | 1/2000 |
| WO | WO 00/00293 |   | 1/2000 |
| WO | WO 00/17630 |   | 3/2000 |

OTHER PUBLICATIONS

Gawad, S., Schild, L. and Renaud, Ph., "Micromachined impedance spectroscopy flow cytometer for cell analysis and particle sizing", Lab on a Chip, 1, 2001, pp. 76-82.*
An article entitled "Radio-Frequency Microtools for Particle and Live Cell Manipulation", By Muller et al., published 1994, pp. 528-535.
An article entitled "Fabrication of a Microfluidic Cell Analyzer . . . ", By Gawad et al., published in Annual International IEEE-EMBS Special Topic Conference on Microtechnologies in Medicine & Biology, Oct. 2000, pp. 1-5.

* cited by examiner

*Primary Examiner*—Nam Nguyen
*Assistant Examiner*—Anthony Fick
(74) *Attorney, Agent, or Firm*—Bachman & LaPointe, P.C.

(57) ABSTRACT

Microtechnologically prepared component as a flow cytometer. The component contains a preparation area to specifically influence and separate the particles, preferably by dielectrophoresis, a measuring channel area for characterizing the particles, and a sorting area for sorting the particles identified in the measuring channel area by dielectrophoresis. The sorting includes switching elements which permit active guidance of the particles into two or more subchannels corresponding to the criteria which have been registered in the measuring channel area. With a component configured in this way for the use of a flow cytometer, quick and precise sorting of particles, in particular biological cells in a suspension, can be implemented.

17 Claims, 4 Drawing Sheets

MICROFLUIDIC COMPONENT AND METHOD FOR SORTING PARTICLES IN A FLUID

BACKGROUND OF THE INVENTION

The present invention relates to a microfluidic component comprising a substrate having a channel for leading individual particles through for sorting particles in a fluid flow, in particular a liquid flow, and also a method for sorting particles.

The manipulation of suspended particles is generally known and is described, for example, by G. Fuhr et al in "Naturwissenschaften" [Natural sciences] volume 81, 1994, page 528 ff. Here, the suspended particles can be any desired particles or else biological cells. In the following text, therefore, in general only particles will be mentioned. The microsystems form in particular channel structures through which a suspension liquid with the particles to be manipulated flow. In the channel structures, microelectrodes are fitted to the channel walls and have high-frequency electric fields applied to them. Under the action of the high-frequency electric fields between two electrodes, polarization forces are produced in the suspended particles on the basis of negative or positive dielectrophoresis, said forces permitting repulsion or attraction by the electrodes and, in interaction with flow forces in the suspension liquid, permitting manipulation of the particles in the channel. Electrodes of this type are described, for example, in WO 00 00 293.

In S. Gawad et al, "1st Annual International IEEE-EMBS Special Topic Conference on Microtechnologies in Medicine & Biology Oct. 12-14, 2000, Lyons, FRANCE:", pages 1 to 5, and also from S. Gawad et al "Lab on a Chip", 2001, 1, pages 76 to 82, it is known to analyze cells in a microchannel by means of impedance spectroscopy. In this case, use is made of electrodes embedded in the channel, so that at least two field areas are produced, in which an impedance measurement is carried out. Evaluation is then carried out by means of a difference measurement, for example by means of a measuring bridge. With regard to further details, reference is made to these publications and the explanations given therein relating to the measuring principle and to the prior art.

The results of such an analysis can then be used to carry out cell sorting next. Here, it is likewise known to carry out cell sorting on the basis of dielectrophoresis. For example, it is known from U.S. Pat. No. 4,326,934 to extract sulfur from oil by means of dielectrophoresis.

U.S. Pat. No. 5,489,506 discloses a method and an apparatus for the continuous sorting of living cells from a mixture, in which the cells passing one or more electrodes are sorted out in accordance with their size, physical construction, chemical composition and electronic characteristics, the electrodes being connected to radio-frequency generators.

In the method described above, the different electrophoretic characteristics for the particles are used to lead these out of the fluid flow. This is passive sorting, since a specific decision as to whether the particles are to be led out or not cannot be made.

The previously known devices for characterizing particles, in particular biological cells, sorting and counting (cytometers) are distinguished by very complicated devices, which generally comprise an optical analysis device based on FACS (fluorescence-activated cell sorting) or a combination of optical and electrical measuring devices. Purely electrical detection and sorting is not carried out. Therefore, in the case of these devices, additional preparation of the particles for the optical analysis is required. This makes the analysis by means of such devices complicated and time-consuming.

It is an object of the present invention to provide an electrical flow cytometer which, on a substrate in micro- or nanotechnology, permits the identification and counting and sorting as quickly and accurately as possible.

SUMMARY OF THE INVENTION

According to the invention, the foregoing object is achieved by a microfluidic component comprising a substrate (a) at least one channel (2) for leading through individual particles (17) in a fluid, the channel (2) comprising: a preparation area (6) to specifically influence and separate the particles (17), a measuring channel area (7) having electrode devices for characterizing the particles (17), and a sorting area (8) having electrode devices for sorting the particles (17) identified in the measuring channel area (7) by means of dielectrophoresis; and (b) conductor tracks (12) which are electrically connected to the electrodes (13, 14', 14", 20-30) in the individual areas (6-8) in order to transmit signals to the electrodes and signals from the electrodes and a method which comprises.

The basic idea of the invention is that, on a carrier material, called a substrate below, in at least one elongate channel through which the individual particles are led in a fluid, said particles are prepared firstly in a first area in the fluid flow for the subsequent measurement in a second measuring channel area and then, after leaving the measuring channel area, the particles are separated in a third area, the sorting area, on the basis of the registered characteristics of the particles. In this case, it is of course possible for the separation to be performed into more than just two different types. Accordingly, the channel comprises a preparation area with first electrode devices to specifically influence and separate the particles, preferably by means of dielectrophoresis. This is followed by the measuring channel area having second electrode devices for characterizing the particles. There then follows the sorting area having third electrode devices for sorting the particles identified in the measuring channel area by means of dielectrophoresis. Of course, on the substrate there are additionally conductor tracks which are electrically connected to the respective electrodes in order to transmit signals to the electrodes and away from the electrodes. For this purpose, the component must be connected to appropriate measurement and control devices, which are not the subject of the invention.

In this case, the cross sections of the individual areas vary in such a way that the cross section of the channel (measuring channel) in the measuring channel area is substantially smaller than the cross section in the preparation area and in the sorting area.

The electrode arrangements used in connection with dielectrophoresis always comprise a pair of identical electrodes which, as a rule, are fitted to the channel walls laterally or at top and bottom, so that in the coincident areas between the individual electrodes an electric field can build up which causes the particles to make the desired movements. In the following text, therefore, the terms electrodes or electrode pair will be used as synonyms.

In order that characterization and subsequent sorting is possible at all, it is necessary in the preparation area to separate the particles, which may possibly cohere in clusters, and then to feed them in a controlled manner to the measuring channel area. This is preferably done by means of corresponding electrode arrangements, so that the particles are separated by means of dielectrophoresis and the forces acting on the particles as a result, and are brought into the appropriate particle path.

According to a preferred development, the electrode devices for separating the particles have electrode arrangements which contain first electrodes arranged obliquely with respect to the flow direction and having a substantially funnel-like arrangement and, following these in the flow direction, spaced-apart parallel second electrodes in a likewise funnel-like arrangement with a passage opening. In this case, the following parallel second electrodes are kept continuously at potential, so that incoming particles are held up and can pass through the passage opening only if they pass through individually. Larger clusters cannot pass through. As a result of the configuration, the passage opening constitutes a narrow slit in the channel. In order to separate the clusters located upstream of the passage opening, the first electrodes are pulsed, so that, on account of the forces which occur as a result, the individual particles attempt to escape and in the process are detached from the other particles. The distance between the electrodes is preferably two to four times the particle diameter.

Following this, the particles are aligned in the fluid flow, so that the particles move on a defined particle path. According to a further preferred embodiment, the first electrode arrangement for separating is directly followed by a second electrode arrangement for aligning the particles onto a defined particle path. The separation electrode arrangement is preferably also combined with the electrode arrangement for alignment, in which the previously mentioned second parallel electrodes having the passage opening have lengthened parallel electrode arms at the spacing of the width of the passage opening (gap). This electrode arrangement therefore comprises two upper electrode arms arranged at the spacing of the gap width and two associated lower electrode arms, in each case a field building up on an associated upper and lower electrode. As a result of arranging four electrode arms, the particles attempt to find the equilibrium state exactly at the center. In this case, it is necessary for the length of the electrode arms, in relation to the flow velocity of the solution, to be sufficiently long in order that the equilibrium state can be reached. The width of the passage opening and the spacing of the electrode arms is slightly greater than the particles.

These particles prepared in this way then pass into the measuring channel area, which preferably has a cross section which is only slightly greater than the particles flowing through. Its typical channel size can be 5 to 10 μm. The passage of a particle, in particular for example of an individual cell, is registered and identified by the change in the electrical impedance which, in the case of a cell, has a relationship with the characteristics of the cell size, cell membrane and the cytoplasma. The above cited article by Gawad et al., is incorporated by reference.

According to another preferred embodiment, a wide measuring channel is used, which has the advantage that the risk of a blockage is reduced. In this wider measuring channel, the individual particles are deflected onto a specific path on one side of the channel by means of dielectrophoresis and then pass through the measuring field between two electrodes, the reference field being arranged in the area in which no particles move.

The dimensions of the channel lie in the order of magnitude of the typical particle size to be measured or an order of magnitude above. The electrodes can be arranged in various ways on the walls, in order to provide at least two detection areas in the same channel. The electrodes can be arranged one after another on one side of the channel, circling around the channel, only above, or above and below or laterally. If the electrodes are arranged one after another only on one side of the channel, there is a great influence on the particle position during the measurement. If the position of the particles is to be determined accurately, it is expedient to perform the measurement by means of a differential measurement between an offset upper and lower electrode pair. This has the effect that, depending on the vertical alignment of the particle, the upper or lower electrodes are influenced more or less. In a corresponding way, this can be carried out on the side walls.

After the individual particles have passed through the measuring channel area, they come into the sorting electrode area having a larger cross section. In order that proper sorting is possible, according to a preferred embodiment, there is upstream of the sorting electrode arrangement an electrode arrangement for aligning the particles, in order to lead the latter onto the narrowest possible path in the fluid flow. This permits exact sorting at high speed, since the corresponding electrodes can have a small electrode length and therefore the path of the sorted particles led out of the particle path is short along the electrodes, and therefore a new selection can be made relatively quickly thereafter.

According to a particularly preferred refinement of the invention, the electrode devices in the sorting area have a first sorting electrode arrangement and at least a second sorting electrode arrangement, the first sorting electrode arrangement being arranged in the path of the particles and the second sorting electrode arrangement being arranged at the side of the paths of the particles in order specifically to lead particles sorted out by the first sorting electrode arrangement onward. The second sorting electrode arrangement preferably has an output to pass the particle, so that the particles sorted out move on a second path, substantially parallel to the first particle path. Following this, a fork is arranged in the channel, which divides the fluid flow in accordance with the particle paths. The substrate therefore has one inlet and at least two outlets. The outlets can then be fed to appropriate holding containers or the like.

In order that observation and detection by means of optical methods is also possible, it is expedient to design the substrate to be transparent.

The substrate according to the invention therefore permits, in the smallest possible space, the determination of individual particles from a large number of particles passing through, of the order of magnitude of 100 or more particles per second. The invention permits the positioning of the particles, the measurement of the impedance, the velocity or the position of the particles flowing in the measuring channel, and a flow switching arrangement in the sorting area, which allows the particles to be led into two or more subchannels in accordance with the previously determined criteria in the measuring area. Such a microtechnological produced component can be used to count cells, to distinguish them and to sort them in accordance with their type, their size, their cell membrane characteristics, the presence and/or the activity of specific membrane receptors. Within the context of the sorting, the identification and counting of particles is therefore also possible.

According to the method for sorting particles in a fluid flow by means of a microfluidic component, the following steps are carried out:

A separating the particles by means of dielectrophoresis and subsequently positioning the particles in the physical center of the fluid flow, B characterizing the separated particles into a narrow fluid flow in a measuring channel area by means of impedance measurement, C sorting the particles registered in the measuring channel area on the basis of the characteristics determined in B by means of dielectrophoresis by actively sorting particles out of the particle path and specifically leading the particles sorted out onward in a second particle path, which runs substantially parallel to the first particle path, D dividing the fluid flow corresponding to the particle paths and E if necessary, repeating steps C and D.

If further subdivision and sorting is to be carried out, steps C and D are repeated appropriately often.

In order to generate the electric fields, preferably one or different voltages with a frequency from 1 kHz to 200 MHz, expediently with peak-to-peak voltages of at most 2 V, are used.

Before sorting, the velocity of the particles is advantageously measured optically or electrically.

In principle, it is possible to carry out the method by means of devices arranged and integrated on the component or else with external devices for field production.

BRIEF DESCRIPTION OF THE DRAWINGS

In order to illustrate the invention further, the latter will be explained in more detail below by using exemplary embodiments in conjunction with the accompanying figures, in which.

DETAILED DESCRIPTION

Figure 1:
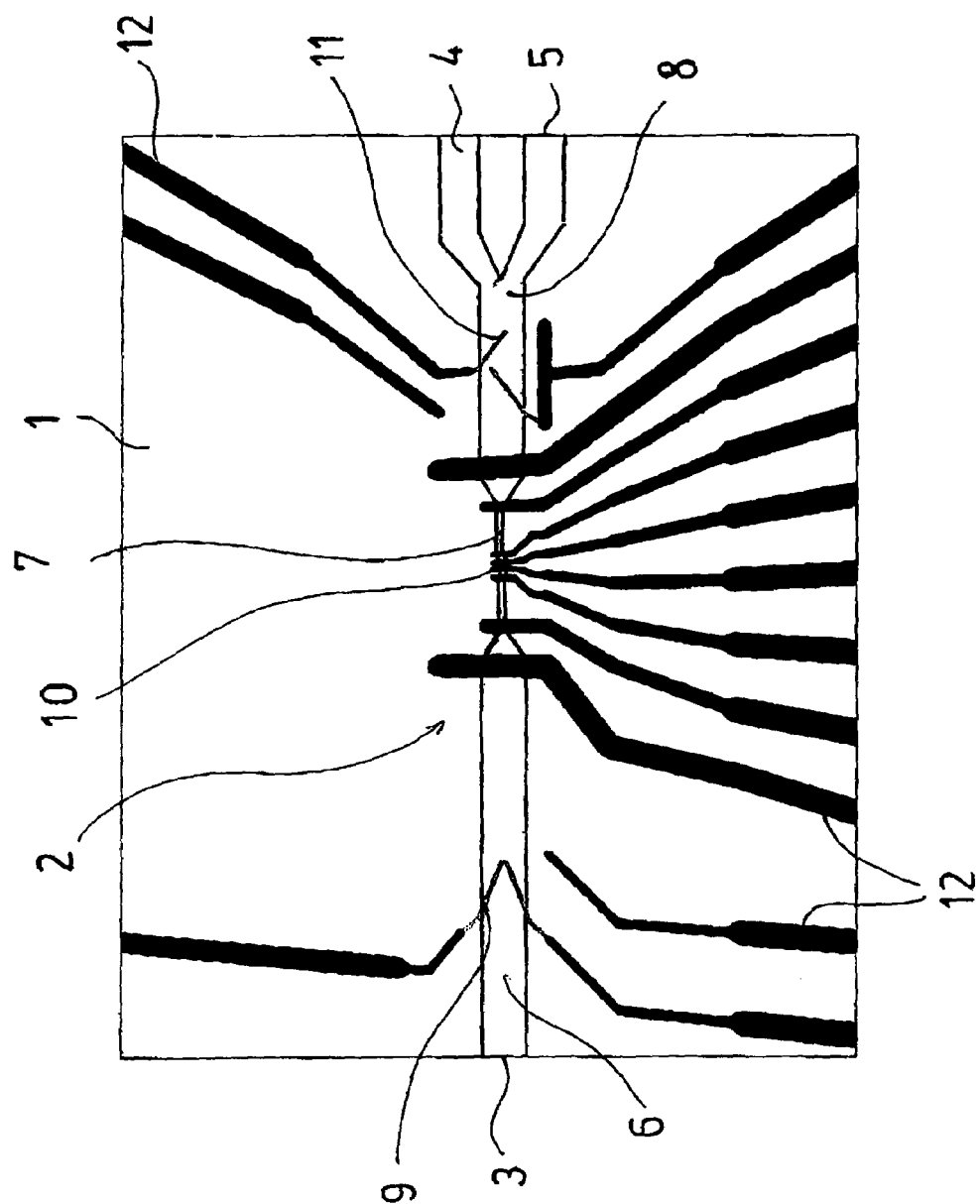
FIG. 1 shows a plan view of a component with a schematic indication of a channel with the individual areas.

The schematic view in FIG. 1 shows a plan view of a microfluidic component 1, which shows an elongate channel 2 which on the left-hand side has an inlet opening 3 and on the right-hand side has two outlet openings 4 and 5. Of course, a corresponding component 1, if necessary, can also have a plurality of outlet openings or else inlet openings. The inlet openings can be connected to appropriately suitable devices for feeding a fluid, which can be liquid or possibly also gaseous. Accordingly, the outlet openings 4 and 5 are also connected to appropriate devices to accommodate the particles sorted out. In the following text, in connection with the exemplary embodiments, a liquid will be assumed, which transports various types of particle, for example biological cells.

The channel 2 is divided into a preparation area 6, a measuring channel area 7 and a sorting area 8. The cross sections of the individual areas are different, in particular the measuring channel area 7 being substantially narrower than the two other areas 6, 8. In the individual areas 6 to 8 there are schematically indicated electrode arrangements 9 to 11, which can be connected via associated conductor tracks 12 to an external control and measurement device, not illustrated. The individual areas with their electrode arrangements are explained further in the following text in connection with the figures.

The production of such a component can be carried out, for example, in that, on a glass substrate, first of all a lift-off resist for defining the positions of the electrodes is applied photolithographically. Following the application of an adhesive layer, for example titanium, a noble metal, for example platinum, as electrode material and a conductor material, for example copper, for a connection of the electrodes, are then deposited. Following the removal of the lift-off resist, polyimide is applied photolithographically as channel walls. The substrate is then joined together with an identical second substrate to form a sandwich structure with enclosed channels and electrodes. The thickness of the platinum layer can in this case be about 200 nm, and the thickness of the titanium layer can be about 50 nm. The polyimide layer is 1 to 20 μm.

It is also possible to use a different material, for example plastic, as the substrate material, and to use replication methods.

Figure 2A:
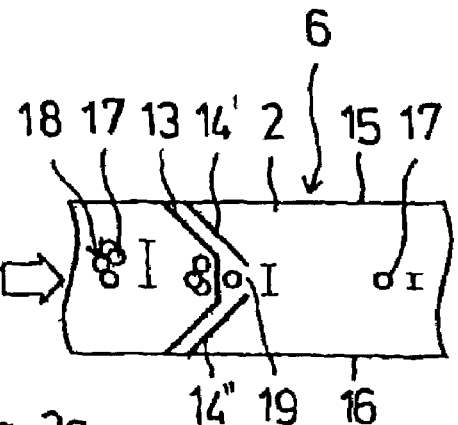
FIG. 2 shows various embodiments and views of arrangements for separating particles, with the plan view of a first arrangement (FIG. 2a), the corresponding sectional illustration in the center of the channel (FIG. 2b), and the plan view of another electrode arrangement for separation (FIG. 2c)
Figure 2B:
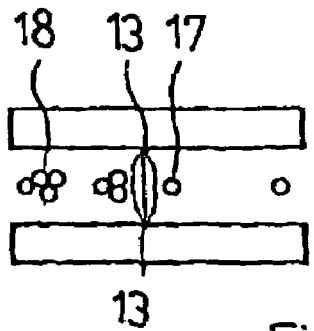

FIG. 2 shows various ways of separating particles. FIG. 2a depicts the plan view of an electrode arrangement having a first separation electrode 13 and second separation electrodes 14' and 14''. The two separation electrodes are arranged obliquely with respect to the walls 15, 16 and, as a result, have a funnel-like shape, which has the effect that the particles 17 or particle clusters 18 moving in this channel area are moved on the basis of the field forces.

In the plan views of the following Figures, as a rule only the upper electrodes are shown. As mentioned previously, in order to influence the particles on the basis of dielectrophoresis, it is obvious that there is also a corresponding lower electrode, which interacts with the upper electrode and therefore builds up the corresponding electric field which has the effect of influencing the particles.

The separation electrodes 13 can of course also be constructed with oblique electrode parts tapering to a point. The electrodes 14', 14'' are arranged obliquely with respect to the walls 15, 16, substantially parallel to the first separation electrode 13. As distinct from the separation electrode 13, they do not touch each other at the end, but leave an opening 19 for the passage of the particles 17. The opening 19 corresponds to the average particle diameter or is slightly larger. The separation electrodes 14' and 14'' are connected permanently and therefore constitute a barrier which holds up the particle clusters 18. The electrode 13 is pulsed and therefore breaks the cluster up. This is shown by way of example in the side illustration according to FIG. 2b. As soon as the particles 17 have been detached from the particle cluster 18, they can pass through the opening 19.

Figure 2C:
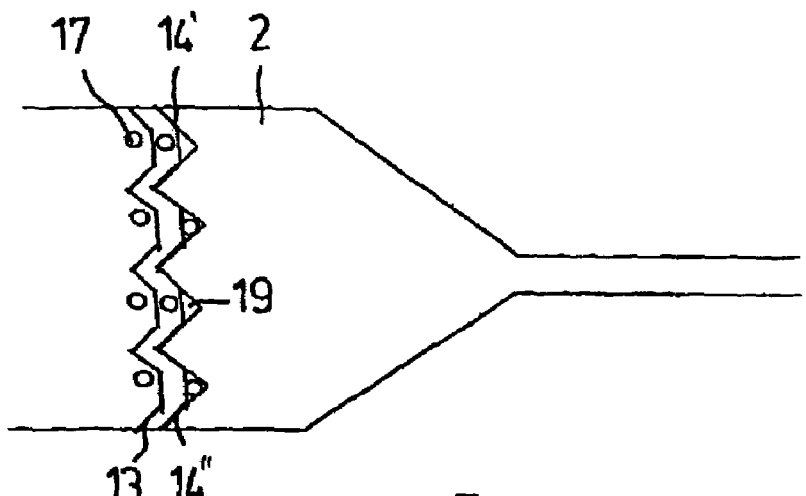

FIG. 2c shows another variant having a different configuration with a plurality of separation electrodes 13 and 14 arranged beside one another. The distance between the separation electrodes 13 and the separation electrodes 14 in all the embodiments is chosen such that it is greater than the particle diameter, but smaller than the particle cluster size to be expected.

Figure 3A:
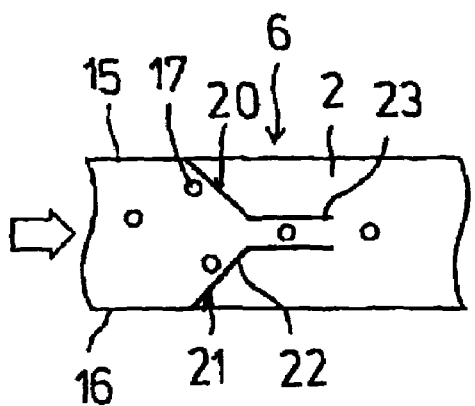
FIG. 3 shows the electrode arrangement for positioning the particles in the fluid flow in plan view (FIG. 3a) and in a lateral sectional illustration (FIG. 3b)
Figure 3B:
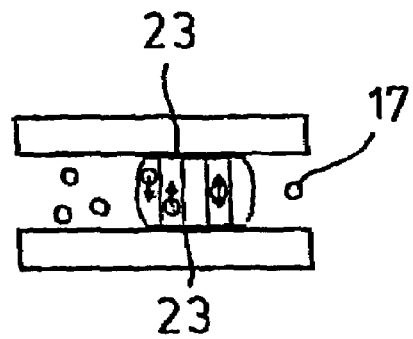

For the subsequent alignment of the particles 17 in a path at a desired position in the channel 2, an electrode arrangement according to FIG. 3a can be used. This figure shows the plan view of funnel-like positioning electrodes 20 and 21 each having an electrode arm 22 running obliquely with respect to the wall 15 and 16 and parallel electrode arms 23. All these electrodes are switched on, the positioning electrode arms 22 having the effect that particles 17 moving in the channel move laterally toward the center. The positioning electrode arms 23 effect the vertical positioning of the particles, as shown in FIG. 3b. It is important here that the length of the parallel positioning electrode arms 23, opposite which, as mentioned above, there are corresponding electrodes on the underside of the channel, is long enough to permit the vertical forces acting on the particles to find an equilibrium state, so that the height of the outlet path of the particles 17 is constant and, in this case, is centered in the channel. As a result of the lower electrodes, there is a total of four electrodes and, since the force on the particles 17 is higher when they approach the electrodes, in the case of a symmetrical electrode design, said electrodes tend to be centered at the center. The spacing of the electrodes should therefore also be chosen such that the particles are influenced by both electric fields (field from the electrode arms 22 and field from the electrode arms 23). The spacing between the positioning electrode arms 22 and 23 is only slightly greater than the particle diameter.

Figure 4:
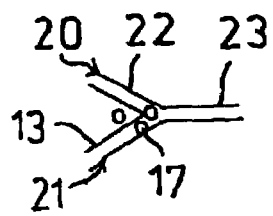
FIG. 4 shows the combination of an electrode arrangement according to FIGS. 2a and 3a in plan view.

FIG. 4 shows an electrode arrangement from the combination of electrodes according to FIG. 3a and FIG. 2a, the pulsed separation electrode 13 in this exemplary embodiment being configured so as to taper to a point. The spacing of the oblique electrode parts is two to four times the particle diameter.

Figure 5A:
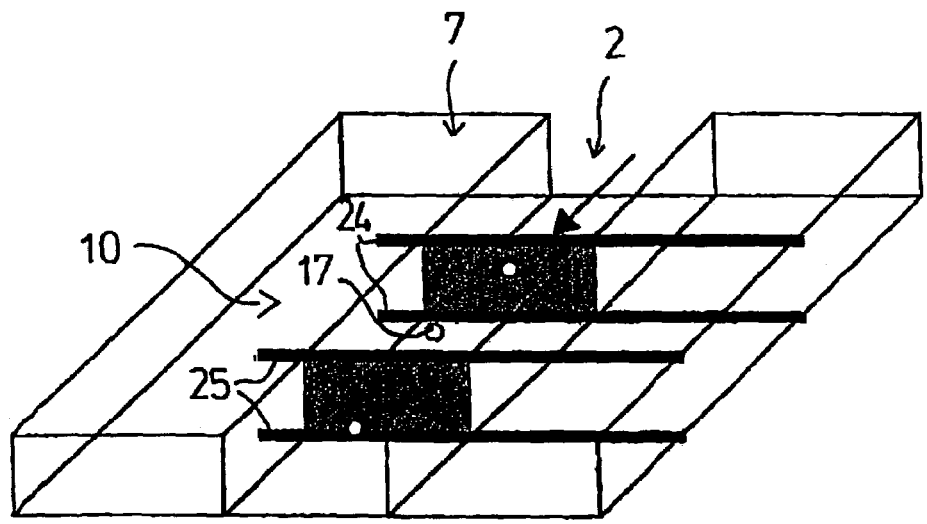
FIG. 5 shows two different electrode arrangements for the measuring channel area, once with a narrow measuring channel (FIG. 5a) and with a wider channel (FIG. 5b)

FIG. 5 shows an exemplary embodiment of the channel 2 in the measuring channel area 7, with an appropriate electrode arrangement 10. The electrode arrangement 10 in this exemplary embodiment comprises, in a known manner, a first electrode pair 24 and a second electrode pair 25, wherein each pair build up an electric field. The liquid and the particles flow through the channel 2 of the measuring channel area 7. For most cases, a liquid contains an electrolyte of an impedance different from the particles. The first 24 and second 25 electrode pairs are connected to an electrical system, not illustrated, which measures the voltage across the individual electrodes and the current through the areas which are formed by the pairs of measuring electrodes 24 and 25. Due to the difference between the impedance of the electrolyte and that of a particle, the measurement and control devices can ascertain when a particle passes through the first 24 or second 25 electrode pair fields. Each time a particle passes through the area of the first measuring electrode pair 24, the aforementioned electrical parameters change. The area of the second measuring electrode pair 25 remains unchanged and serves as a reference. The behavior is appropriately reversed when a particle 17 passes through the second measuring electrode pair 25. Using the first 24 and second 25 electrode pair impedance measurements, the velocity of a particle in the measuring channel area 7 may be obtained.

By way of background, velocity is the rate of change of displacement from a fixed point The average velocity v of a particle moving a distance d in a straight line during a time interval t is described by $$v = \frac{d}{t}. \tag{1}$$

The distance d between the first 24 and second 25 electrode pairs in the measuring channel area 7 is known and the time t a particle passes from the first electrode pair 24 to the second electrode pair 25 may be derived by the measurement and control devices. The measurement and control devices may therefore yield velocity.

The change in the electrical parameters is measured at the same time at a plurality of alternating current frequencies, which permits better differentiation and more accurate determinations of the parameters. The measured parameters are used by a control and measuring device, not illustrated, to carry out the subsequent sorting.

Figure 5B:
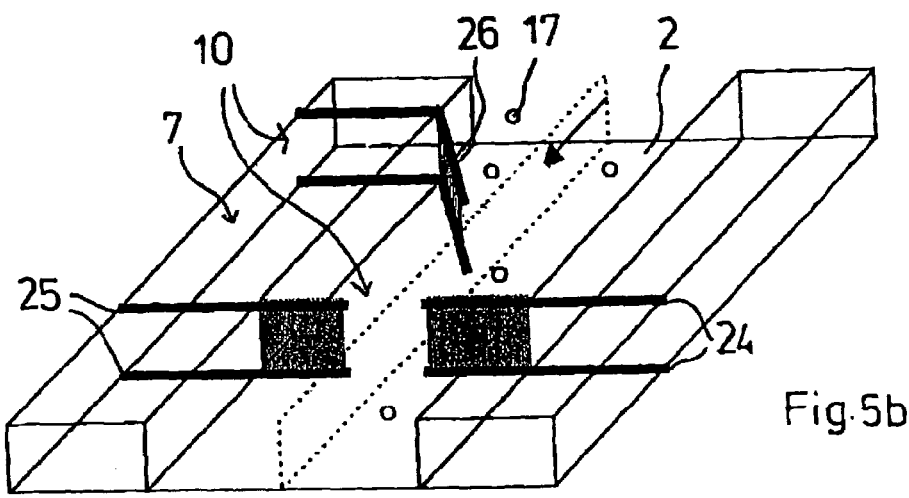

FIG. 5b shows a different configuration having a wider channel 2 in the measuring channel area 7, a pair of deflection electrodes 26 deflecting the incoming particles 17 to a specific particle path, which leads through the measuring electrode pair 24. The measuring electrode pair 25 is arranged in the area of the channel in which there are no particles 17. The measuring electrode pair 25 therefore always serves as a reference. This configuration has the advantage that the risk of blockage is reduced by the greater channel width. Nevertheless, the measurement can be carried out by means of correspondingly small configurations of the electrodes as in FIG. 5a, in spite of an enlarged channel width. The electric fields are therefore concentrated in relation to the particle sizes, that is to say the influence of a large particle on the field is greater than the influence of a smaller particle. The measurements therefore become more accurate if the particle covers the greatest possible area of the field. The associated measurement electronics are neither shown nor further explained here (in this regard, see the aforementioned article by S. Gawad).

Figures 6A, 6B:
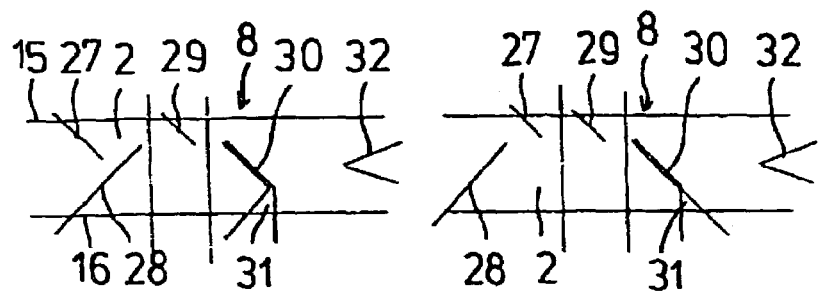
FIG. 6 shows various electrode arrangements for the alignment and sorting in the sorting area, having a first geometric arrangement (FIG. 6a), a second, different geometric arrangement (FIG. 6b), a third geometric arrangement of only the electrodes for leading away the particles sorted out (FIG. 6c), and the arrangement according to FIG. 6a in an enlarged illustration with the path of the particles (FIG. 6d).

FIG. 6 shows various electrode arrangements 11 in the sorting area 8. This electrode arrangement permits fast sorting of the particles. FIG. 6a shows two alignment electrodes 27, 28, which bring the particles 17 coming from the measuring channel in the exemplary embodiment into an area in the vicinity of one wall 15 of the channel 2. Both alignment electrodes 27, 28 are switched on. The electrode 29 is the actual sorting electrode which, depending on whether a particle 17 is to remain on the path predefined by the alignment electrodes 27 and 28, is switched off or else, if the particle 17 is to be deflected, is switched on. The deflection electrode 30 carries the deflected particles away and, owing to an opening 31, permits the particle to emerge, so that division of the particles 17 in the direction of the two outlet openings 4 and 5 according to FIG. 1 is possible by means of the following fork 32. FIG. 6b shows another alternative arrangement of the alignment electrodes 27 and 28, the electrode 27 being designed to be shorter than the following sorting electrodes 29 and serving to carry the particles 17 away from the wall 15. The deflection electrode 30 exhibits a different geometric arrangement here, as an example, without influencing the output result. In FIGS. 6a and 6b, in the case of the deflection electrode, both the electrodes, that is to say the upper and lower electrode, are illustrated in parallel, in order to illustrate the fact that the desired guidance of a particle 17 takes place only in the area in which the lower and the upper deflection electrode are illustrated as parallel. In the remaining area, the opening 31 for the passage is produced.

Figure 6C:
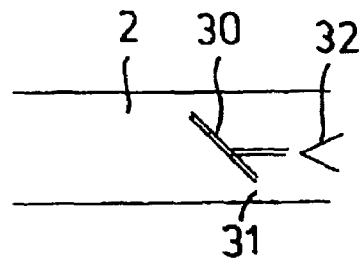

FIG. 6c shows a further possible configuration of the deflection electrode pair 30.

Figure 6D:
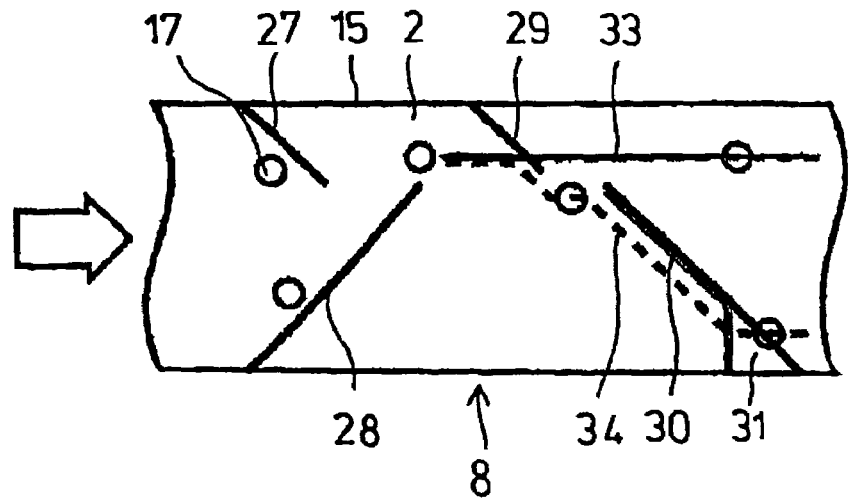

The sorting operation will be explained in more detail by using FIG. 6d. It shows two possible paths for the particles 17. As already mentioned, the alignment electrodes 27, 28 and the deflection electrodes 30 are always switched on. The sorting electrode pair 29 is activated when a particle is to be sorted out. This has the effect that the particle is deflected out of the intrinsically provided particle path 33 and is moved along the particle path 34 by the fluid flow. The deflection electrodes 30 do not overlap on the same section, so that, as a result, they form an opening 31 for the particles, which can then move onwards on a path substantially parallel to the particle path 33. In order to achieve fast sorting, it is important for the length of the sorting electrode 29 to be as short as possible but long enough that, when it is switched on, the particle 17 continues its path toward the electrode 30 and the action of switching off the sorting electrode pair 29 for the next particle can be carried out as soon as possible. The deflection electrode 30 is arranged in such a way that particles which are not sorted out by the sorting electrode 29 can continue their path without being influenced too greatly by the deflection electrode 30.

For the processes controlled by means of dielectrophoresis, voltages in the region of 10 V and frequencies from 100 kHz to 10 MHz are used, depending on the liquid and the particles. For the measurements in the measuring channel, the voltage is less than 2 V and the frequencies are 10 kHz to 200 MHz.

With the microfluidic component described above, integrated, fast and cost-effective "on-chip" detection with subsequent division is possible.

The invention claimed is:

1. A microfluidic component comprising a sandwich structure having at least one channel (2), each channel (2) having at least one inlet (3) and at least two (4, 5) outlets, for leading through individual particles (17) in a fluid flow, the channel (2) comprising:
   a preparation area (6) to specifically influence and separate the particles (17), by means of dielectrophoresis;
   a measuring channel area (7) having at least two sensing areas arranged in series with respect to the fluid flow direction with each sensing area having electrode devices for characterizing each particle (17) by measuring particle impedance in each sensing area and particle (17) velocity; and
   a sorting area (8) having electrode devices for sorting particles (17) identified in the measuring channel area (7) in relation to the measured particle (17) velocity by means of dielectrophoresis; wherein the cross section of the sensing areas in the measuring channel area (7) is substantially smaller than the cross section in the preparation area and in the sorting area (6 and 8), and conductor tracks (12) which are electrically connected to the electrodes (13, 14', 14", 20-30) in the individual areas (6-8) in order to transmit signals to the electrodes and signals from the electrodes.

2. The component as claimed in claim 1, wherein the particles (17) are influenced by dielectrophoresis in the preparation area (6) by means of electrode devices, the first electrode devices having electrode arrangements which first separate the particles (17) and then keep them in a specific position in the fluid flow.

3. The component as claimed in claim 2, wherein the electrode arrangements (9) for separating the particles (17) have first electrodes (13) arranged obliquely with respect to the flow direction and having a substantially funnel-like arrangement and, following these in the flow direction, second electrodes (14', 14"), parallel with the first electrodes (13), in a likewise funnel-like arrangement with a passage opening (19).

4. The component as claimed in claim 2, wherein the electrode arrangements (9) for positioning have electrodes (20,21) which keep the particles (17) at the center of the fluid flow.

5. The component as claimed in claim 4, wherein the electrode arrangements (9) have electrodes (20,21) arranged in a funnel shape with electrode arms (22) which are arranged obliquely with respect to the fluid flow direction and form a central passage opening (19) and, directly adjacent thereto, at a distance from the passage opening (19), have electrode arms (23) that run in parallel, the first electrode arms (22) serving to align the particles (17) in a plane in the center of the fluid flow, and the second electrode arms (23) to align the particles (17), one after the other along a center line of the plane.

6. The component as claimed in claim 5, wherein the second electrode arms (23) have a length which is sufficient to permit the forces acting on the particles (17) in the interspace between the electrodes to position the particles in the center line of the plane.

7. The component as claimed in claim 1, wherein the distance between the electrodes (13, 14', 14"), is two to four times the particle diameter.

8. The component as claimed in claim 1, wherein the electrode devices in the sorting area (8) have a first sorting electrode arrangement (29) and at least a second sorting electrode arrangement (30), the first electrode arrangement (29) being arranged in the path (33) of the particles (17) and the second sorting electrode arrangement (30) being arranged at the side of the path of the particles in order to guide particles (17) sorted out by the first sorting electrode arrangement (29) in the flow direction.

9. The component as claimed in claim 8, wherein the second sorting electrode arrangement (30) is arranged obliquely with respect to the flow direction and has an output (31) for the passage of the particle (17).

10. The component as claimed in claim 9, wherein, after the second sorting electrode arrangement (30), a fork (32) is arranged in the channel (2) of the sorting area (8) defining first (4) and second (5) outlets.

11. The component as claimed in claim 8, wherein in the sorting area (8) in the path of the particles (17) upstream of the first sorting electrode arrangement (29) there is arranged an electrode arrangement (27,28) for aligning the particles (17), which arrangement guides the particles (17) coming from a measuring channel area (7) sensing area onto the narrowest possible path in the fluid flow, and the electrodes of the first sorting electrode arrangement (29) are arranged obliquely in the path of the particles and have a length which substantially corresponds to the width of the path.

12. A method for sorting particles in a fluid flow by means of a microfluidic component comprising:
    separating the particles (17) by means of dielectrophoresis and subsequently positioning the particles in the physical center of the fluid flow;
    characterizing the separated particles into a narrow fluid flow in at least two measuring channel area (7) channel sensing areas by means of impedance measurement by generating at least two electric fields (24,25) in the measuring channel and, by comparing the at least two electric fields (24,25), information about the size, electrical characteristics, and velocity of the particles is determined;

sorting the particles by means of dielectrophoresis registered in the measuring channel area (7) on the basis of the characteristics by actively sorting particles out of the first particle path (33) in relation to the velocity of the particles and specifically leading the particles sorted out in a flow direction in a second particle path (34), which runs substantially parallel to the first particle path (33); and dividing the particle paths (33,34).

13. The method as claimed in claim 12, wherein different voltages with a frequency from 1 kHz to 200 MHz are used to generate the electric fields.

14. The method as claimed in claim 12, wherein the peak-to-peak voltages are at most 2 V.

15. The method as claimed in claim 12, wherein, before sorting, the velocity of the particles is measured optically or electrically.

16. The method as claimed in claim 12, wherein, before sorting, the particles are guided onto a particle path in the fluid flow.

17. The method as claimed in claim 16, wherein particles are subsequently led out of the particle path (33) by setting up or removing a first electric field barrier (29) and are led along a further field barrier (30) onto a particle path (34) substantially parallel to the first particle path (33), and the fluid flow is subsequently divided in accordance with the two particle paths (33,34).

* * * * *